United States Patent [19]

Wirth et al.

[11] Patent Number: 4,835,310

[45] Date of Patent: May 30, 1989

[54] REACTION PRODUCTS OF BISGLYCIDYL THIOETHERS

[75] Inventors: Hermann O. Wirth, Bensheim; Rainer Schneider, Zwingenberg; Hans-Helmut Friedrich, Lautertal, all of Fed. Rep. of Germany

[73] Assignee: Ciba-Geigy Corporation, Ardsley, N.Y.

[21] Appl. No.: 25,231

[22] Filed: Mar. 12, 1987

[30] Foreign Application Priority Data

Mar. 13, 1986 [CH] Switzerland ............. 1020/86

[51] Int. Cl.$^4$ .............. C10M 129/08; C07C 149/18; C07C 149/24
[52] U.S. Cl. ........................... 252/47.5; 564/501; 568/44; 568/46; 568/50; 252/48.2; 252/49.3; 252/77
[58] Field of Search .............. 564/501; 568/44, 46, 568/50; 252/47.5, 48.2

[56] References Cited

U.S. PATENT DOCUMENTS

| 2,731,437 | 1/1956 | Bender et al. ............. 525/483 |
| 4,153,729 | 5/1979 | Warolin et al. ............. 564/501 |

FOREIGN PATENT DOCUMENTS

| 166696 | 5/1986 | European Pat. Off. ............. 568/46 |
| 2172284 | 9/1986 | United Kingdom . |

OTHER PUBLICATIONS

C.A., 104, 209908n (1986).
C.A., 105, 225770n (1986).

Primary Examiner—Glennon H. Hollrah
Assistant Examiner—Susan P. Treanor
Attorney, Agent, or Firm—Harry Falber; Luther A. R. Hall

[57] ABSTRACT

1. Compounds of the formula I

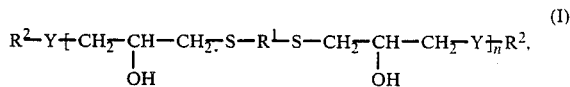

in which n is a number from 1 to 100, Y is $-N(R^3)-$, $-S-$ or $-S-R^4-S-$, $R^1$ is $C_2-C_8$-alkylene, which can be interrupted by 1 to 3 ether oxygen atoms, $R^2$ is hydrogen, unsubstituted or hydroxyl-monosubstituted to -pentasubstituted $C_1-C_8$-alkyl, which can be interrupted one or more times by $-O-$, $-S-$ or $-N(R^5)-$ as long as $R^2$ is not unsubstituted $C_1-C_8$-alkyl when Y is $-S-$ and n is 1, $R^3$ is hydrogen unsubstituted or hydroxylmonosubstituted to -pentasubstituted $C_1-C_8$-alkyl, which can be interrupted one or more times by $-O-$, $-N(R^5)-$ or $-S-$, $R^4$ is unsubstituted or OH-monosubstituted or -polysubstituted $C_2-C_8$-alkylene, which can be interrupted one or more times by $-O-$ or $-S-$, are very highly suitable for use as high pressure and antiwear additives for polar functional fluids.

14 Claims, No Drawings

REACTION PRODUCTS OF BISGLYCIDYL THIOETHERS

The present invention relates to novel reaction products of bisglycidyl thioethers, to the use thereof in polar functionally fluids, in particular those based on water, and to such functional fluids as contain these novel reaction products.

Oxygen-containing bisglycidyl thioethers are described in U.S. Pat. No. 2,731,437 as liquid polymers for preparing gels, resins or rubbers.

The present invention provides compounds of the formula I

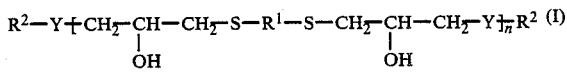

in which n is a number from 1 to 100, Y is $-N(R^3)-$, $-S-$ or $-S-R^4-S-$, $R^1$ is $C_2-C_8$-alkylene, which can be interrupted by 1 to 3 ether oxygen atoms, $R^2$ is hydrogen, unsubstituted or hydroxyl-monosubstituted to -pentasubstituted $C_1-C_8$-alkyl, which can be interrupted one or more times by $-O-$, $-S-$ or $-N(R^5)-$ as long as $R^2$ is not unsubstituted $C_1-C_8$-alkyl when Y is $-S-$ and n is 1, $R^3$ is hydrogen, unsubstituted or hydroxylmonosubstituted tp -pentasubstituted $C_1-C_8$-alkyl, which can be interrupted one or more times by $-O-$, $-N(R^5)-$ or $-S-$, $R^4$ is unsubstituted or OH-monosubstituted or -polysubstituted $C_2-C_8$-alkylene, which can be interrupted one or more times by $-O-$ or $-S-$, and $R^5$ is defined in the same way as $R^3$ except that it is not alkyl interrupted by heteroatoms.

A $C_2-C_8$-alkylene $R^1$ can be straight-chain or branched, preferably straight-chain, for example ethylene, propylene, trimethylene, tetramethylene, pentamethylene, 2,2-dimethyl-1,3-trimethylene, hexamethylene, heptamethylene or octamethylene.

A $C_2-C_8$-alkylene $R^1$ which is interrupted by 1 to 3 ether oxygen atoms is for example 2-oxa-1,3-propylene, 2,4-dioxa-1,5-pentylene, 2,5,8-trioxa-1,9-nonylene, 2,5,8-trioxa-1,11-undecylene or 2,9-dioxa-1,10-decylene.

$C_1-C_8$-alkyls $R^2$ and $R^3$ are straight-chain or branched alkyl, for example methyl, ethyl, n-propyl, isopropyl, n-butyl, isobutyl, sec.-butyl, tert.-butyl, straight-chain or branched pentyl, hexyl, heptyl, or octyl.

In $C_1-C_8$-alkyls $R^2$ and $R^3$ substituted by 1 to 5 hydroxyl groups the C atom which is directly bonded to Y preferably carries no OH group.

In $C_1-C_8$ alkyl $R^2$ and $R^3$ interrupted one or more times by $-O-$, $-S-$ or $-N(R^5)-$, the hetero atoms can be present in every possible position.

A $C_2-C_8$-alkylene $R^4$ can be straight-chain or branched, preferably straight-chain, for example ethylene, propylene, trimethylene, tetramethylene, 2,2-dimethyl-1,3-trimethylene, hexamethylene, heptamethylene or octamethylene.

In OH-monosubstituted or -polysubstituted $C_2-C_8$-alkylene $R^4$, the OH substitutes can be present in every possible position.

$C_2-C_8$-alkylene $R^4$ interrupted one or more times by $-O-$ or $-S-$ is for example 2-oxa-1,3-propylene, 2,4-dioxa-1,5-pentylene, 3,5-dioxa-1,6-hexylene, 3-oxa-1,6-hexylene, 3,6-dioxa-1,8-octylene, 2,5,8-trioxa-1,9-nonylene, 2,5,8-trioxa-1,11-undecylene, 2,9-dioxa-1,10-dedylene, 2-thia-1,3-propylene, 2,4-dithia-1,5-pentylene, 3-thia-1,6-hexylene or 2,5,8-trithia-1,11-undecylene, Preference is given to compounds of the formula I in which n is $>1$.

A further embodiment relates to compounds of the formula I in which Y is $-N(R^3)-$.

Special interest attaches to compounds of the formula I in which $R^3$ is hydroxyl-monosubstituted to -pentasubstituted $C_1-C_8$-alkyl which can be interrupted one or more times by $-N(R^5)-$.

Particular interest attaches to compounds of the formula I in which $R^3$ is hydroxyl-pentasubstituted $C_6$-alkyl.

Very particular interest attaches to compounds of the formula I in which Y is $-N(R^3)-$ or $-S-$, $R^1$ is $C_2-C_8$-alkylene in particular ethylene, $R^2$ is hydrogen, unsubstituted or hydroxyl-monosubstituted to -pentasubstituted $C_1-C_6$-alkyl which can be interrupted by 1-3 $-O-$ or $-S-$ groups, and $R^3$ is hydrogen or hydroxyl-monosubstituted to -pentasubstituted $C_1-C_8$-alkyl, with the proviso that when Y is $-S-$ and n is 1, $R^2$ cannot be unsubstituted $C_1-C_8$-alkyl.

The degree of polymerization n is known to be expressable, at least semiquantitatively, in terms of viscosity in the sense that the higher the molecular weight, the higher the viscosity.

Particular preference is given to compounds of formula I, in particular to those in which Y is $-N(R^3)-$, $R^3$ being hydroxyl-pentasubstituted $C_6$-alkyl, and n has a value such that the kinematic viscosity of a 50% solution in water at 40° C. is 20-50 mm²/s.

Very special preference is given to compounds of the formula I in which n has a value such that the kinematic viscosity of a 50% solution in water at 40° C. is 25-35 mm²/s.

Particular preference is given to compounds of the formula I in which n has a value such that the kinematic viscosity of a 50% solution in water at 40° C. is 27-30 mm²/s.

Examples of compounds of the formula I are:

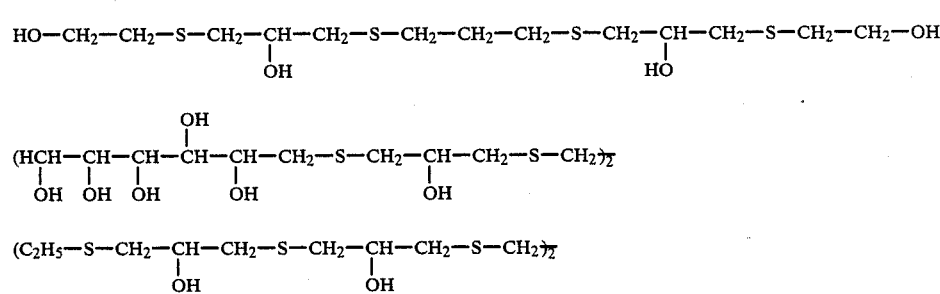

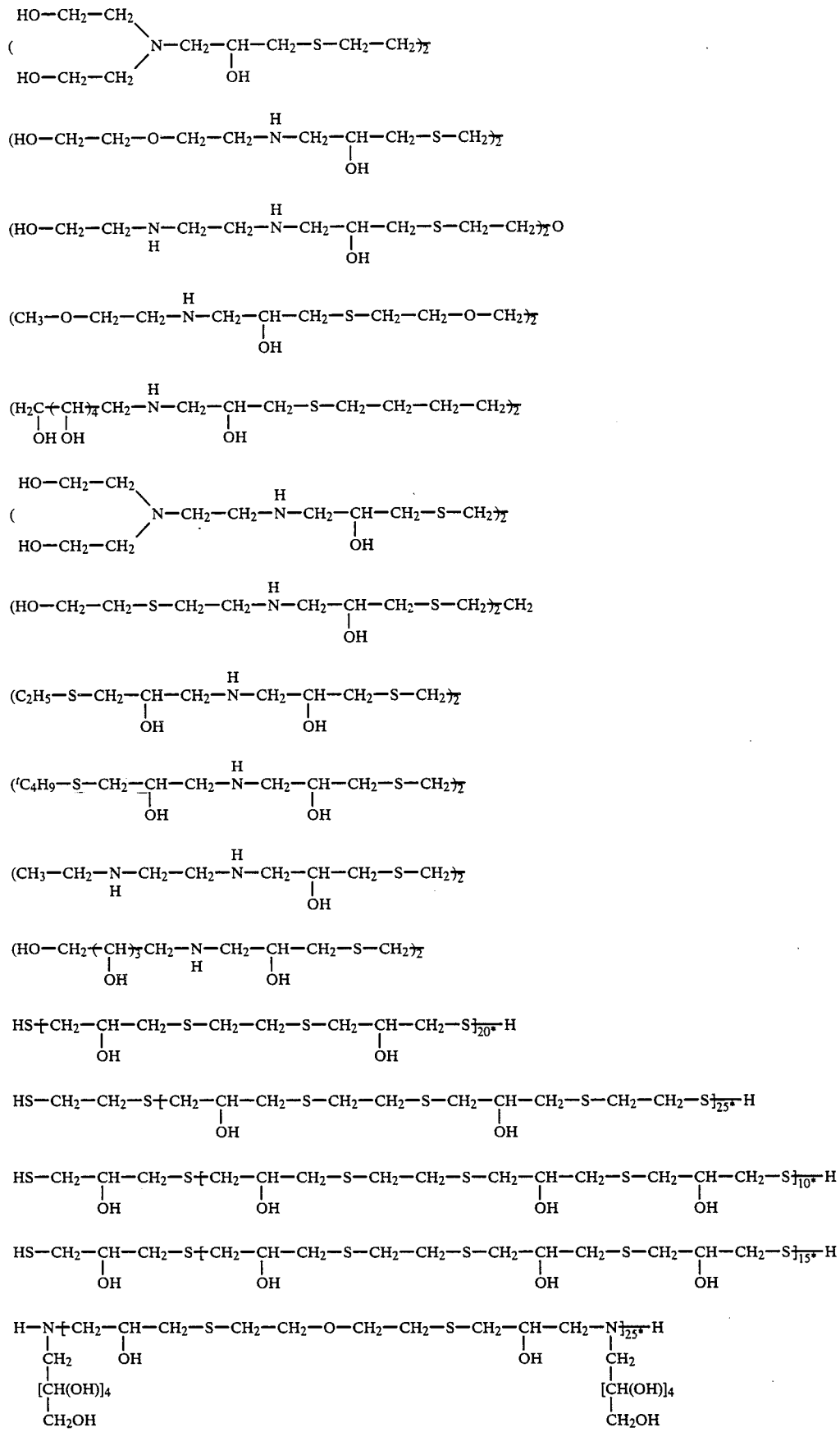

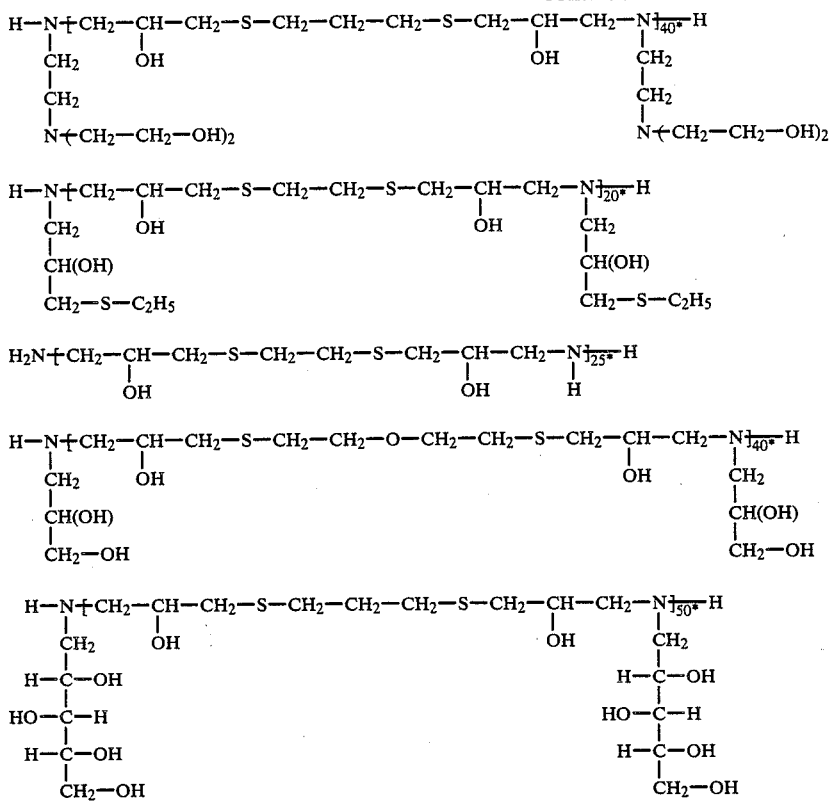

*These numbers are statistical averages, i.e. the products consist of a polymolecular mixture and the indicated number is an average.

The compounds of the formula I can be prepared in a manner known per se, for example by reacting appropriate bisglycidyl thioethers, the preparation of which is described for example in EP-A-166,695, with mercaptans or amines.

The invention also relates to reaction products obtainable from the reaction of bisglycidyl thioethers of the formula

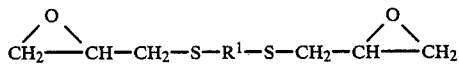

with compounds of the formula H—Y—R$^2$, in which Y is —N(R$^3$)—, —S— or —S—R$^4$—S—, R$^1$ is C$_2$-C$_8$-alkylene, which can be interrupted by 1 to 3 ether oxygen atoms, R$^2$ is hydrogen, unsubstituted or hydroxyl-monosubstituted to -pentasubstituted C$_1$-C$_8$-alkyl, which can be interrupted one or more times by —O—, —S— or —N(R$^5$)—, R$^3$ is hydrogen, unsubstituted or hydroxyl-monosubstituted to -pentasubstituted C$_1$-C$_8$-alkyl, which can be interrupted one or more times by —O—, —N(R$^5$)— or —S—, R$^4$ is unsubstituted or OH-monosubstituted or -polysubstituted C$_2$-C$_8$-alkylene, which can be interrupted one or more times by —O— or —S—, and R$^5$ defined in the same way as R$^3$ except it is not alkyl interrupted by hetero atoms, the reaction being carried out in such a way that in the case of Y=S and R$^2$=unsubstituted C$_1$-C$_8$-alkyl the reaction product contains at least 2 bisglycidyl thioether units per molecule, and also to process for preparing compounds of the formula I and the above-described reaction products, which comprises reacting a bisglycidyl thioether of the formula

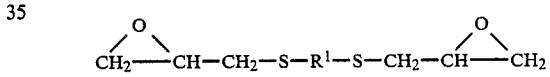

with a compound of the formula H—Y—R$^2$, the general symbols being defined as above.

Equations (1) and (2) illustrate the addition reactions in the case of two general examples.

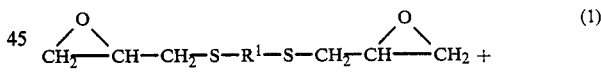 (1)

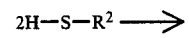

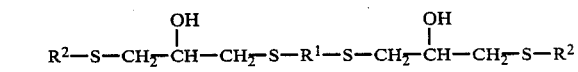

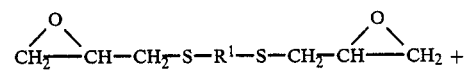 (2)

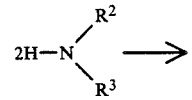

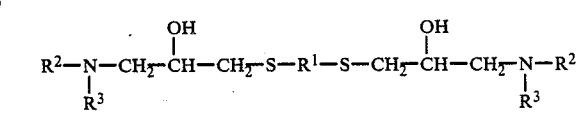

The preferred reaction media are water, methanol or ethylene glycols or polyethylene glycols or mixtures of the last three with water.

Advantageously the procedure adopted is such that, ideally, the result is a high end-product concentration suitable for confectioning. Expediently, the reaction media are identical to the functional fluids or are constituents thereof into which the end products can be introduced (see below).

In certain cases, the reactants can be reacted as such without use of a reaction medium.

The addition reaction with mercaptans is expediently to be catalyzed with inorganic bases (e.g. potassium hydroxide), or alternatively, tertiary amines. The addition reaction can even be carried out at room temperature; however, by working at higher temperatures, for example at 50°–70° C., the length of reaction can be significantly shortened.

The addition reaction with amines generally requires no catalysis. To ensure an adequate rate of reaction, it is expedient to work at elevated temperatures, for example at 50°–80° C.

Compounds of the formula I in which n has a value $>1$ are prepared in a similar way. It may be emphasized once more than n is a statistical average, since these polyadditions give rise to products which are characterized by a molecular weight distribution. In this case, a bisglycidyl thioether is reacted with a bismercaptan of the formula $H-S-R^4-S-H$ or $H_2S$ or with a sterically unhindered primary amine of the formula $H_2N-R^3$, the two reactants being used in a molar ratio of 1:1.

By predetermining the stoichiometric ratio of the two bifunctional components it is possible to affect n. A molar ratio other than 1:1 always leads to a reduced n.

Suitable macromolecule-terminating end groups are the free SH or NH groups, of which the former predominate when the educt is predominantly bismercaptan and the latter if the educt is predominantly amine.

The novel compounds of the formula I are very good high pressure and antiwear additives for polar functional fluids. They also contribute, at least indirectly, to corrosion inhibition. Finally, the higher molecular weight representatives can also be used as thickeners (viscosity enhancers).

The novel compounds of the formula I are polar by nature, i.e. they are substances having polar solubility characteristics. The compounds of the formula I can be used in polar functional fluids, in particular those based on water, ethylene glycol, diethylene glycol, polyethylene glycol and blends thereof with water, in a homogeneous solution state. Similarly, they can also be used in functional fluids based on phosphoric acid esters, preferably aryl phosphates. But even colloidal systems are industrially very useful, in particular on account of their favourable dispersing and emulsifying properties, for example for the preparation of emulsions and microemulsions.

The compounds of formula I can specifically also be used in polar functional fluids of complex structure with water as predominant base liquid, in particular fluids having a water content of at least 50% by weight, with or without the presence of low molecular weight glycol compounds, for example ethylene glycol, diethylene glycol or thiodiethylene glycol, and further with phosphoric acid as well as a base for setting the pH between 7.5 and 12, preferably at 8.5, as further components.

Bases for pH control are for example alkali metal hydroxides, preferably potassium hydroxide, water-soluble organic bases, preferably alkanolamines, in particular ethanolamine. Polymeric amines, for example polyethyleneimine, can also be used for pH control.

The aforementioned functional fluid of complex structure can also contain as further components fatty acids, preferably oleic acid, and, if desired, boric acid as well.

The polar functional fluids of complex structure can additionally contain additives which are added to improve the basic properties of these functional fluids even further; they include: corrosion inhibitors, foam breakers, softeners and biocides.

Examples of corrosion inhibitors are as follows:

(a) organic acids, their esters, ammonium, amine, alkanolamine and metal salts, for example benzoic acid, p-tert.-butylbenzoic acid, disodium sebacate, triethanolamine laurate, isononanoic acid, triethanolamine salt of p-toluenesulfonamidocaproic acid, triethanolamine salt of benzenesulfonamidocaproic acid, triethanolamine salts of 5-ketocarboxylic acid derivatives as described in EP-A-41,927, sodium N-lauroylsarcosinate or nonylphenoxyacetic acid.

(b) nitrogen-containing substances such as fatty acid alkanolamides, imidazolines, for example 1-hydroxyethyl-2-oleylimidazoline, oxazolines, triazoles, for example benzotriazoles or Mannich base derivatives thereof, triethanolamines, fatty amines, inorganic salts, for example sodium nitrate, and the carboxytriazine compounds described in EP-A-46,139.

(c) Phosphorus-containing substances such as amine phosphate, phosphonic acids or inorganic salts, for example sodium dihydrogenphosphate or zinc phosphate.

(d) Sulfur-containing compounds such as sodium, calcium or barium petroleumsulfonates or heterocyclic compounds such as sodium mercaptobenzthiazole.

It is also possible to use complexing agents, such as nitrilotriacetic acid and salts thereof, foam-breaking agents such as silicones, for example polydimethylsiloxanes, distearylsebacamide, distearyladipamide and similar products derived from ethylene oxide and/or propylene oxide condensations, addition products of fatty alcohols, such as capryl alcohols and condensation products thereof with ethylene oxide, furthermore biocides such as e.g. amine, quaternary ammonium compounds, chlorophenols, sulfur-containing compounds, such as sulfones, methylene bisthiocyanates and biscarbamates, isothiazolones, bromopropionamides, triazines, phosphonium compounds, chlorine and chlorine-denoting substances and organometallic compounds such as tributyl tin oxide.

A particular advantage of the compounds according to the invention is their hydrolytic stability. For that reason they exhibit an extremely low pH sensitivity.

Viscosity-enhancing action of the polyadducts may be especially mentioned once more; this too is a very favourable aspect, since polar functional fluids having a very high water content necessitate the use of a viscosity-enhancing additive (thickener).

For the use of compounds of formula I in hydraulic fluids, the presence of an additional thickener as a further component is advantageous.

Suitable thickeners are for example polyalkylene oxides, polyalkyl methacrylates, polyamide esters, polyamide alkoxylates or polyethyleneimines which can at the same time perform all or part of the function of a pH regulator.

The amount of thickener used is expediently between 2 and 50% by weight, preferably between 5 and 15% by weight, based on the base liquid.

The amount used of compounds of the formula I is for example 0.5 to 10% by weight, based on the total amount of polar functional fluid.

If the compounds of the formula I are used in functional fluids of complex structure, they are expediently used in an amount of 0.5-2% by weight, preferably 0.5-1% by weight, based on the total amount of functional fluid of complex structure, the total amount of additives preferably accounting for 0.5-10% by weight, preferably 2.5-5% by weight, based on the water content thereof.

Polar functional fluids and in particular those based on water, ethylene glycol, diethylene glycol, polyethylene glycol and blends thereof with water or on phosphoric acid esters, as well as functional fluids or complex structure can be used for example as hydraulic fuids, metal processing fluids, cooling fluids or drilling fluids, in particular as hydraulic fluids.

The present invention also relates to a composition containing a polar functional fluid, in particular on the basis of water, ethylene glycol, diethylene glycol, polyethylene glycol and blends thereof with water or of phosphoric acid esters, or a functional fluid of complex structure and at least one compound of the formula I.

The following examples illustrate the invention in more detail. Percentages and parts, as in the rest of the description and in the claims, are by weight, unless otherwise stated.

EXAMPLE 1

Addition product of glucamine onto 1,2-bis(glycidylmercapto)ethane

Stage 1: 1,2-bis(glycidylmercapto)ethane

A 1 l SOVIREL ® reactor (a jacketed reaction vessel) equipped with a thermometer, stirrer, dropping funnel, meterable dropping funnel and pH electrode is charged with 141 g of 1,2-dimercaptoethane and 4 g of tetrabutylammonium chloride. To this solution are added dropwise in the course of 200 minutes with water cooling and stirring 278 g of epichlorohydrin at pH 9.9-10.1. The pH is kept constant throughout the entire period of 200 minutes by metered addition of 20% aqueous sodium hydroxide solution (consumption about 8 ml). The reaction temperature should not exceed 20° C.

After the exothermic reaction has ended, 530 ml of 20% sodium hydroxide solution are added dropwise in the course of 15 minutes, the reaction mixture is subsequently stirred at 40° C. for 20 minutes, and finally the aqueous phase is sharply separated off. The remaining organic phase is the bisepoxide.

The yield is 293 g (95% of theory) with a refractive index of $n_D^{20}$ of 1.5430 and an epoxy content of 96.5 mol-%.

Stage 2:

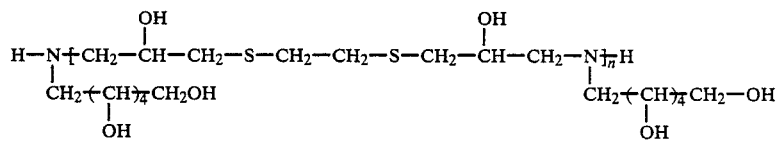

32.2 g of glucamine are dissolved in 77.4 g of distilled water. To this solution are added dropwise at 60°-70° C. with stirring in the course of 45 minutes 41.2 g of 1,2-bis(glycidylmercapto)ethane; a strongly exothermic reaction results. The mixture is subsequently stirred at the same temperature for 30 minutes.

Yield: 154.8 g ≙ 100% of theory of a yellowish viscous liquid having a refractive index (measured on a 50% solution in water) of $n_D^{20}$: of 1.4455 and a viscosity at 40° C. of 27-30 mm²/s (likewise 50% solution in water).

EXAMPLE 2

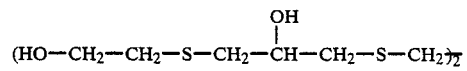

To 14.1 g of 2-mercaptoethanol are added catalytic amounts of sodium methylate, the mixture is heated to 60°-70° C. with stirring, and after the heating bath has been removed 20.6 g of 1,2-bis(glycidylmercapto)ethane are added dropwise at the same temperature to give a strongly exothermic reaction. On completion of the addition the mixture is subsequently stirred at 70° C. for 30 minutes.

Yield: 34.2 g ≙ 100% theory, crystalline mass $n_D^{50}$: 1,5940

EXAMPLES 3-10

Stage 2 of Example 1 is repeated to prepare the compounds of Examples 3-9, and Example 2 is repeated to prepare the compound of Example 10.

| Example | Formula | Physical data |
|---|---|---|
| 3 | (HO—CH₂—CH₂—NH—CH₂—CH(OH)—CH₂—S—CH₂)₂ | 50% in H₂O $n_D^{20}$: 1.4390 |
| 4 | (HO—CH₂)₂—C(CH₂OH)—NH—CH₂—CH(OH)—CH₂—S—CH₂)₂ [HO—CH₂, HO—CH₂ substituents on C] | 50% in H₂O $n_D^{20}$: 1.4372 |
| 5 | (CH₂(OH)—CH(OH)—CH(OH)—CH(CH₃)—CH₂—N—CH₂—CH(OH)—CH₂—S—CH₂)₂ with OH on fourth C | 50% in H₂O $n_D^{20}$: 1.4376 |

-continued

| Example | Formula | Physical data |
|---|---|---|
| 6 | $(CH_2-CH-CH-CH-CH-CH_2-N-CH_2-CH-CH_2-S-CH_2)_{\overline{n}}$ with OH, OH, OH, OH on first part, $C_2H_5$ on N, OH on CH | 50% in $H_2O$; $n_D^{20}$: 1.436 |
| 7 | $HO-CH_2-CH_2\diagdown N-CH_2-CH(OH)-CH_2-S-CH_2)_{\overline{n}}$ / $HO-CH_2-CH_2$ | $n_D^{20}$: 1.542 |
| 8 | $H-N+CH_2-CH(OH)-CH_2-S-CH_2-CH_2-S-CH_2-CH(OH)-CH_2-N)_{\overline{n}}H$ with $(CH_2)_3-N(CH_2-CH_2-OH)_2$ branches | 50% in $H_2O$; $n_D^{20}$: 1.4447 |
| 9 | $H-N+CH_2-CH(OH)-CH_2-S-CH_2-CH_2-S-CH_2-CH(OH)-CH_2-N)_{\overline{n}}H$ with $CH_2-CH_2-OH$ branches | $n_D^{50}$: 1.5755 |
| 10 | $CH_2-S-CH_2-CH_2-S-CH_2-CH(OH)-CH_2+S(CH_2-CH_2-O)_{\overline{2}}CH_2-CH_2-SH$ / $HO-CH$ \ $CH_2-S+CH_2-CH_2-O)_{\overline{2}}CH_2-CH_2-S)_{\overline{n}}H$ | $n_D^{50}$: 1.5768 |

EXAMPLE 11

The Shell four ball machine (IP 239/73 Extreme pressure and wear lubricant test for oils and greases) is used to determine the following values:

1. W.L.=weld load in newton (N). This is the load at which the 4 balls weld together within 10 seconds.
2. W.S.D.=wear scar diameter in mm; this is the average wear scar diameter on exposure to a load of 400N for 10 minutes.

The test fluid used for this test of efficacy is deionized water.

| Additive of Example No. | W.L. (N) 2.5% of additive | W.S.D. (mm) 2.5% of additive |
|---|---|---|
| 1 | 2200 | 0.65 |
| 2 | 2000 | 0.65 |
| 3 | 2000 | 0.76 |
| 4 | 1800 | 0.75 |
| 5 | <1600 | 0.77 |
| 6 | 1400 | 0.75 |
| 7 | <1400 | 0.60 |
| 8 | 2000 | 0.73 |

EXAMPLES 12-14

The following functional fluids of complex structure are prepared:

TABLE 1

| Composition | Example 12 | Example 13 | Example 14[1] |
|---|---|---|---|
| Water | 97.50% | 97.25% | 94.50% |
| Phosphoric acid | 0.63% | 0.80% | 0.70% |
| Boric acid | 0.06% | — | — |
| Ethanolamine | 0.87% | — | 0.88% |
| KOH | — | 0.87% | — |
| Oleic acid | 0.16% | 0.18% | 0.15% |
| Compound of Example 1, Stage 2 | 0.87% | 0.90% | 0.77% |

TABLE 1-continued

| Composition | Example 12 | Example 13 | Example 14[1] |
|---|---|---|---|
| Polyalkylene glycol (thickener) | — | — | 3.00% |

Viscosity at 40° C.: 20.9 cSt.

EXAMPLE 15

In accordance with Example 11, the weld load in N and the wear scar diameter in mm are determined with the Shell four ball machine using as test fluids the functional fluids of Examples 12 to 14.

TABLE 2

| Composition of Example No. | WL (N) | WSD (mm) |
|---|---|---|
| 12 | 2400 | 0.50 |
| 13 | 4000 | 0.50 |
| 14 | 2800 | 0.63 |

We claim:
1. A compound of the formula I

$$R^2-Y+CH_2-CH-CH_2-S-R^1-S-CH_2-CH-CH_2-Y\!\!\!+_{\overline{n}}R^2, \quad (I)$$
$$\phantom{R^2-Y+CH_2-}OH\phantom{CH_2-S-R^1-S-CH_2-}OH$$

in which n is a number from 2 to 100, Y is $-N(R^3)-$, $-S-$ or $-S-R^4-S-$, $R^1$ is $C_2-C_8$-alkylene, which can be interrupted by 1 to 3 ether oxygen atoms, $R^2$ is hydrogen, unsubstituted or hydroxyl-monosubstituted to -pentasubstituted $C_1-C_8$-alkyl, which can be interrupted one or more times by $-O-$, $-S-$ or $-N(R^5)-$ as long as $R^2$ is not unsubstituted $C_1-C_8$-alkyl when Y is $-S-$ and n is 1, $R^3$ is hydrogen, unsubstituted or hydroxylmonosubstituted to -pentasubstituted $C_1-C_8-$ alkyl, which can be interrupted one or more times by —O—, —N(R$^5$)— or —S—, R$^4$ is unsubstituted or OH-monosubstituted or -polysubstituted C$_2$-C$_8$-alkylene, which can be interrupted one or more times by —O— or —S—, and R$^5$ is defined in the same way as R$^3$ except that it is not alkyl interrupted by heteroatoms.

2. A compound according to claim 1, where, in the formula I, Y is —N(R$^3$)—.

3. A compound according to claim 2, where, in the formula I, R$^3$ is hydroxyl-monosubstituted to -pentasubstituted C$_1$-C$_8$-alkyl which can be interrupted one or more times by —N(R$^5$)—.

4. A compound according to claim 3, where, in the formula I, R$^3$ is hydroxyl-pentasubstituted C$_6$-alkyl.

5. A compound according to claim 1, where, in the formula I, Y is —N(R$^3$)— or —S—, R$^1$ is ethylene, R$^2$ is hydrogen unsubstituted or hydroxyl-monosubstituted to -pentasubstituted C$_1$-C$_6$-alkyl which can be interrupted by 1 to 3 —O— or —S— groups, and R$^3$ is hydrogen or hydroxyl-monosubstituted to -pentasubstituted C$_1$-C$_8$-alkyl, with the proviso that when Y is —S— and n is 1, R$^2$ cannot be unsubstituted C$_1$-C$_6$-alkyl.

6. A compound according to claim 1, where, in the formula I, n has a value such that the kinematic viscosity of a 50% solution in water at 40° C. is 20–50 mm$^2$/s.

7. A compound according to claim 1, where, in the formula I, n has a value such that the kinematic viscosity of a 50% solution in water at 40° C. is 25–35 mm$^2$/s.

8. A compound according to claim 1, where, in the formula I, n has a value such that the kinematic viscosity of a 50% solution in water at 40° C. is 27–30 mm$^2$/s.

9. A composition containing a polar functional fluid and at least one compound of the formula I according to claim 1.

10. A composition according to claim 9, wherein the polar functional fluid is a functional fluid based on water, ethylene glycol, diethylene glycol, polyethylene glycol and blends thereof with water or on phosphoric acid esters or has a complex structure.

11. A composition according to claim 10, wherein, in the functional fluid of complex structure, the water content is at least 50% by weight and wherein in phosphoric acid and a base for setting the pH between 7.5 and 12 are present as further components.

12. A composition according to claim 11, wherein the functional fluid of complex structure additionally contains oleic acid and boric acid.

13. A composition according to claim 9, wherein the amount used of compound of the formula I is 0.5–10% by weight.

14. A reaction product obtainable by reacting in a 1:1 molar ratio a bisglycidyl thioether of the formula

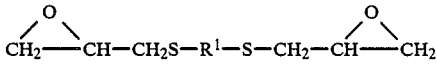

with a compound of formula H—Y—R$^2$ in which Y is —N(R$^3$)—, —S— or —S—R$^4$—S—, R$^1$ is C$_2$-C$_8$-alkylene, which can be interrupted by 1 to 3 ether oxygen atoms, R$^2$ is hydrogen, R$^3$ is hydrogen, unsubstituted or hydroxyl-monosubstituted to -pentasubstituted C$_1$-C$_8$-alkyl, which can be interrupted one or more times by —O—, —N(R$^5$)— or —S—, R$^4$ is unsubstituted or OH-monosubstituted or -polysubstituted C$_2$-C$_8$-alkylene, which can be interrupted one or more times by —O— or —S—, and R$^5$ is defined in the same way as R$^3$ except it is not alkyl interrupted by heteroatoms.

* * * * *